US00PP34773P3

(12) United States Plant Patent
Barba

(10) Patent No.: US PP34,773 P3
(45) Date of Patent: Nov. 29, 2022

(54) GRAPEVINE PLANT NAMED 'INIA-G3'

(50) Latin Name: ***Vitis vinifera* L.**
Varietal Denomination: INIA-G3

(71) Applicant: Instituto de Investigaciones Agropecuarias, Santiago (CL)

(72) Inventor: Paola Barba, Santiago (CL)

(73) Assignee: INSTITUTO DE INVESTIGACIONES AGROPECUARIAS, Santiago (CL)

( * ) Notice: Subject to any disclaimer, the term of this patent is extended or adjusted under 35 U.S.C. 154(b) by 0 days.

(21) Appl. No.: 17/124,887

(22) Filed: Dec. 17, 2020

(65) Prior Publication Data

US 2022/0201912 P1 Jun. 23, 2022

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./156, 206, 207, 205
See application file for complete search history.

*Primary Examiner* — Karen M Redden
(74) *Attorney, Agent, or Firm* — Greer, Burns & Crain, Ltd

(57) ABSTRACT

A new and distinct grapevine variety denominated 'INIA-G3'. The new grapevine is characterized by producing muscat flavored berries, that are ovoid, red, with firm texture, small seed traces and midseason ripening. The clusters are abundant in the vine, large in size and naturally loose, with good keeping and shipping quality.

6 Drawing Sheets

Latin name: *Vitis vinifera* L.
Varietal denomination: 'INIA-G3'.

BACKGROUND

The present invention relates to the discovery and asexual propagation of a new variety of grapevine, *Vitis vinifera* L. denominated 'INIA-G3'. This new cultivar resulted from controlled hybridization between 'Moscatel Rosado' (♀, unpatented) and 'Emperatriz' (♂, U.S. Plant Pat. No. 5,833) performed at latitude 33°35°58'02"S 72°18'56"O, corroborated by molecular markers techniques. The maternal parent 'Moscatel Rosado' was emasculated and hand pollinated with pollen from 'Emperatriz'. Plants were produced from maternal parent 'Moscatel Rosado' seeds. Specifically, the seeds were germinated and planted in Cauquenes, Chile. The new variety 'INIA-G3' was selected and asexually propagated from dormant cuttings in Cauquenes, Chile. In 2006, 'INIA-G3' was introduced to latitude 33°34'18"S, 70°37'46"W for its agronomical characterization.

SUMMARY

'INIA-G3' produces firm, ovoid, red berries with muscat flavor. Berries are small-medium in size reaching about 3.8 gr. Berry size can be moderately increased with application of gibberellic acid. Berries are mostly seedless, but in occasions could develop rudimentary soft seed traces of medium size. The clusters are abundant in the vine, large in size, conical and loose in density. After cluster pruning for exportation, they usually reach 550 g. The fruit has an export market potential for having good keeping and shipping quality. Vines are vigorous and strong. Because its high bud fruitfulness at the basal buds, spur pruning may be used.

'INIA-G3' is most similar to 'Moscatel seedless' (unpatented). 'INIA-G3' differs from this variety by having berries with firmer pulp. It also differs by having bigger and looser clusters. 'INIA-G3' is different from its maternal parent 'Moscatel Rosado' by having rudimentary seeds instead of complete seeds. INIA-G3 differs from its paternal parent 'Emperatriz' by berry clusters as INIA-G3 clusters are more abundant and less variable in berry size. The new variety also has a better shipping and storage quality. 'INIA-G3' could also be compared with 'Crimson Seedless' (unpatented), but differs by having smaller berries and muscat flavor.

The new 'INIA-G3' variety has shown to maintain its distinguishing characteristics through successive asexual propagation by, for example, cuttings.

BRIEF DESCRIPTION OF THE FIGURES

The drawings of the 5-year old grapevine of the present invention are color photographs as follows.

DETAILED BOTANICAL DESCRIPTION

Figure 1:
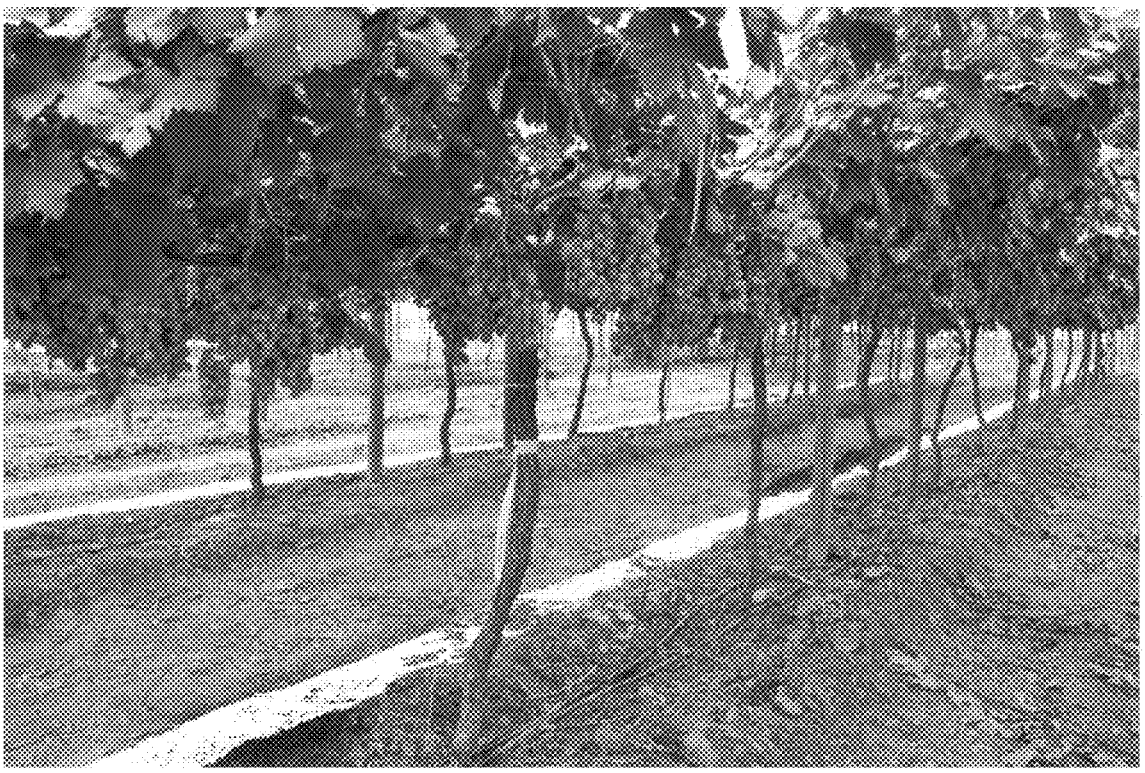
FIG. 1 is a picture of a mature 5-year old plant.
Figure 2:
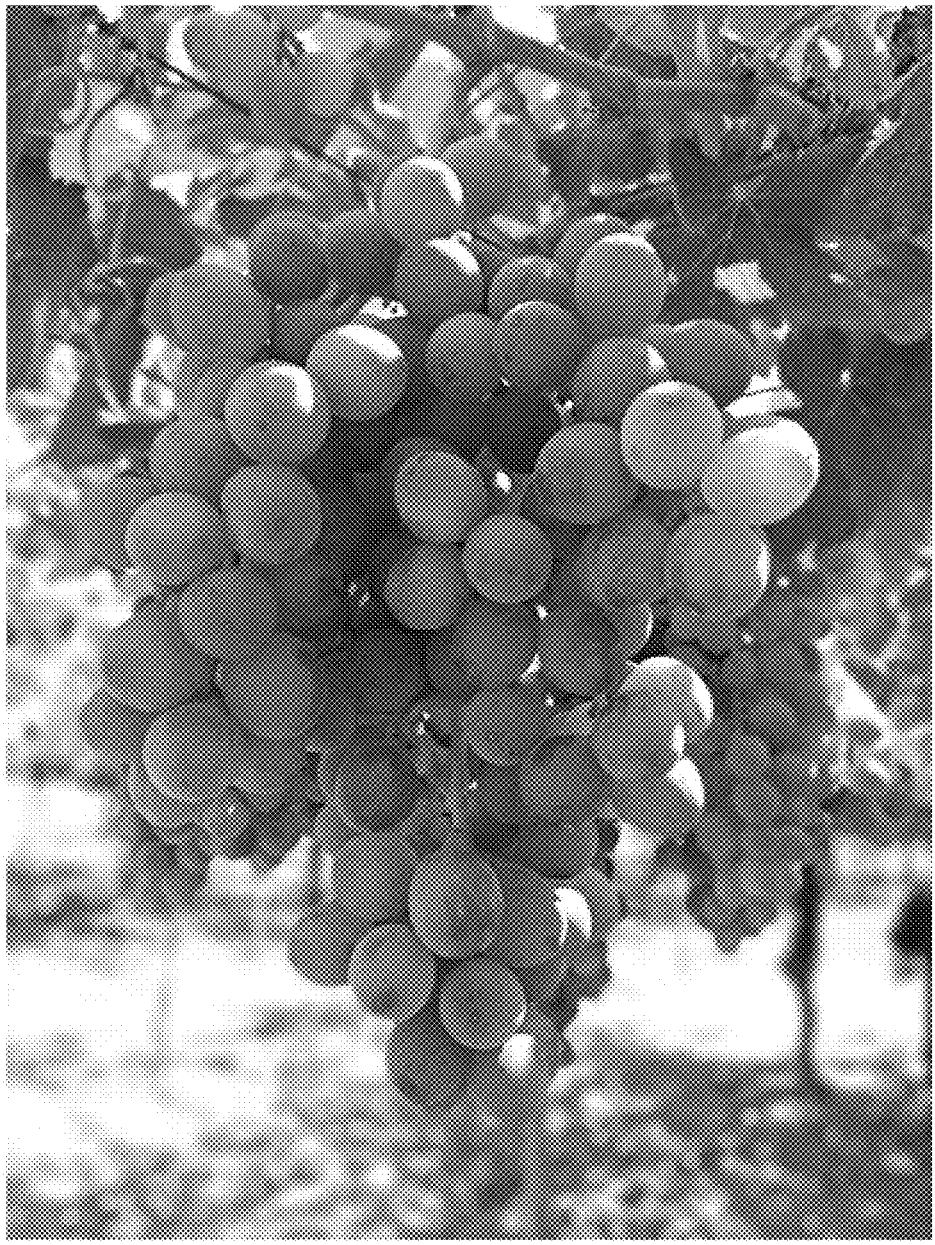
FIG. 2 is a picture of a mature commercially handled cluster.
Figure 3:
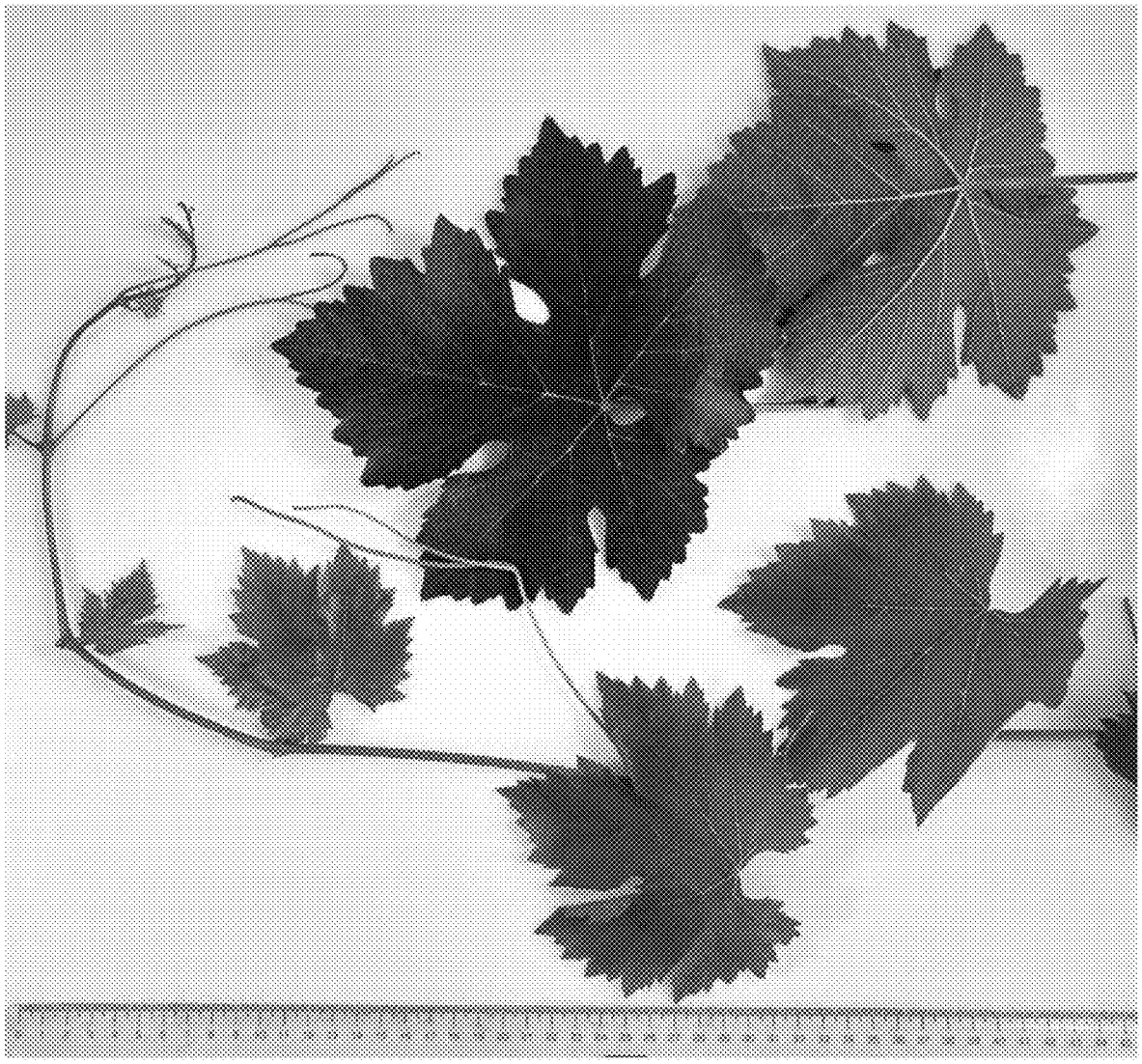
FIG. 3 is a picture with a mature leaf on the top, and a young shoot tip at the bottom.
Figure 4:
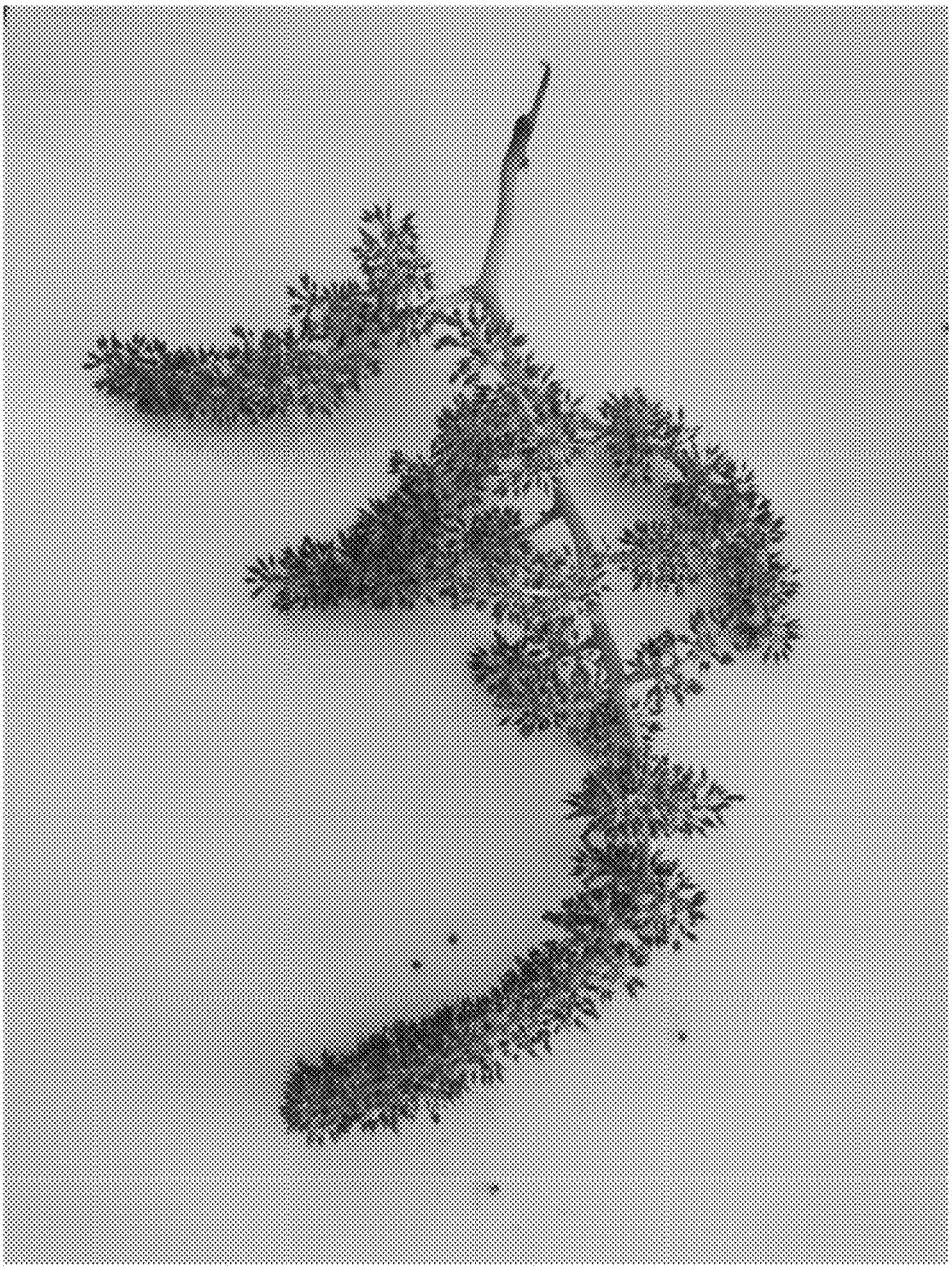
FIG. 4 is a picture of a flowering shoot with flower clusters.
Figure 5:
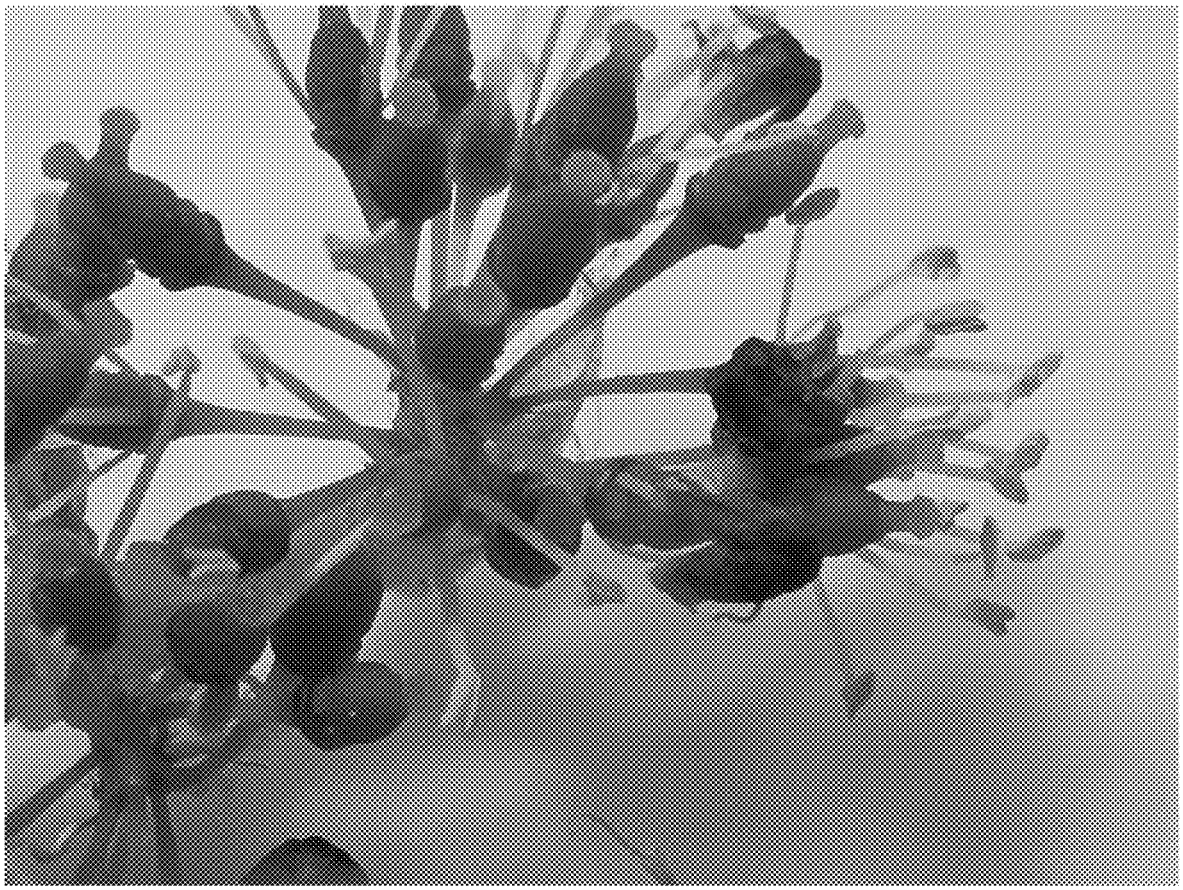
FIG. 5 is a picture zooming at a flower cluster.
Figure 6:
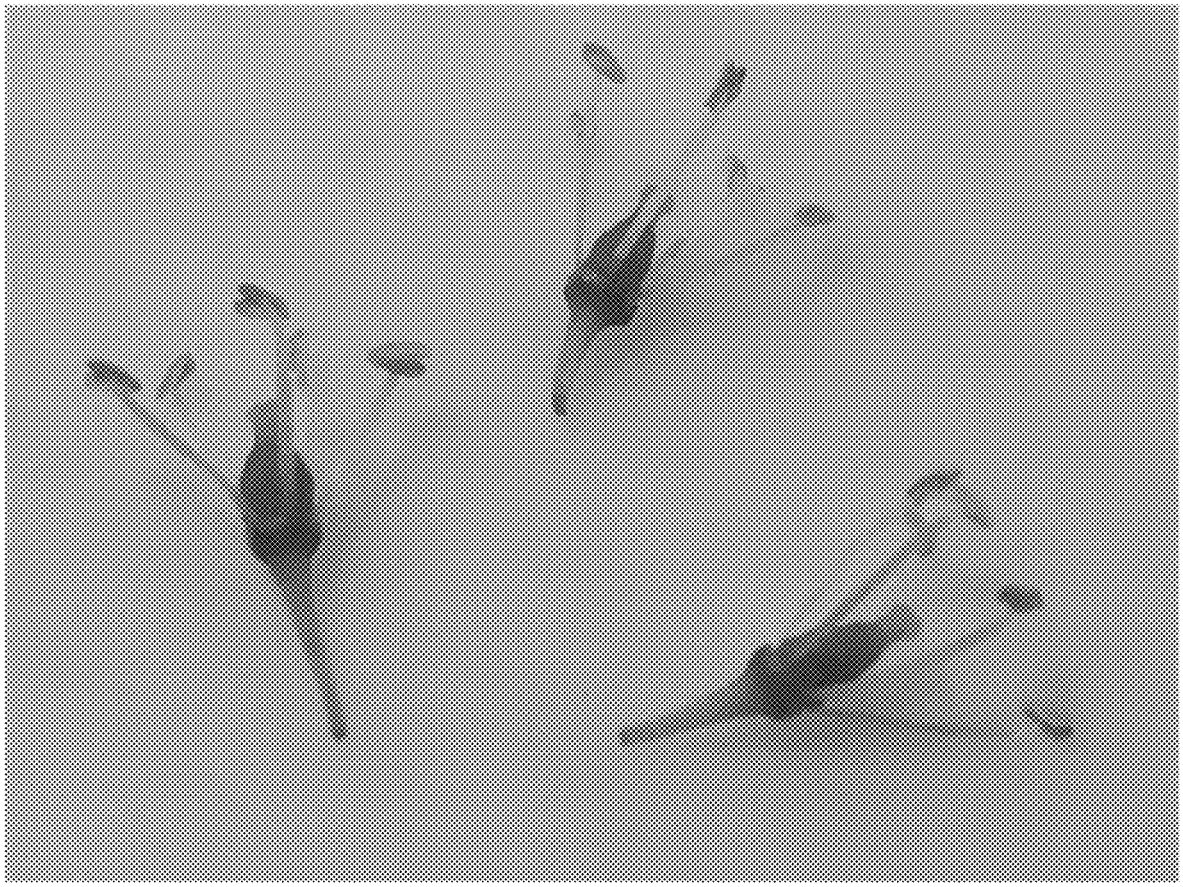
FIG. 6 is a picture of three individual flowers.

The following botanical description represents observations in years 2019 and 2020 from 'INIA-G3' 5-year old plants located in La Platina (33°34'18"S, 70°37'46"W), Santiago, Central valley of Chile.

Colors are described using The R.H.S. Colour Chart 6$^{th}$ Edition, published by The Royal Horticultural Society in 2015. Categorical descriptors were taken from the Union for the Protection of New Varieties (UPOV) document TG/50/9. The descriptive data was taken from commercial handled clusters.

LEAVES

Young leaves:

*Color of upper surface of first 4 distal unfolded leaves.*—Yellow-green 146A.

*Color of lower surface of first 4 distal unfolded leaves.*—Yellow-green 146B.

*Density of prostrate hairs between veins at lower surface of 4th distal unfolded leaf.*—Absent.

*Density of erect hairs between veins at lower surface of 4th distal unfolded leaf.*—Absent.

*Density of prostrate hairs on veins at lower surface of 4th distal unfolded leaf.*—Absent.

*Density of erect hairs between veins at lower surface of 4th distal unfolded leaf.*—Absent.

Mature leaves:

*Color of upper surface.*—Green NN137A.

*Color of lower surface.*—Green 137B and 137C.

*Average length.*—About 18 cm.

*Average width.*—About 18.5 cm.

*Size of blade.*—Medium.

*Shape of blade.*—Pentagonal.

*Number of lobes.*—5.

*Anthocyanin coloration of main veins on the upper side of the blade.*—Absent.

*Mature leaf profile.*—Undulate.

*Blistering surface of blade upper surface.*—Absent or very weak.

*Shape of teeth.*—Mixture of both sides straight and both sides convex.

*Length of teeth.*—Average length of the teeth: 0.88 cm.

*Ratio length/width of teeth.*—Medium.

*General shape of petiole sinus.*—Lobes slightly overlapped.

*Tooth at petiole sinus.*—Absent.

*Petiole sinus limited by veins.*—Absent.

*Shape of upper lateral sinus.*—Lobes slightly overlapped.

*Depth of upper lateral sinus.*—Average depth of the upper lateral sinus is 2.8 cm.

*Density of prostrate hairs between veins on lower surface of blade.*—Absent or very sparse.

*Density of erect hairs between veins on lower surface of blade.*—Absent or very sparse.

*Density of prostrate hairs on main veins on lower surface of blade.*—Absent or very sparse.

*Density of erect hairs on main veins on lower surface of blade.*—Absent or very sparse.

*Density of prostrate hairs on main veins on upper surface of blade.*—Absent or very sparse.

FLOWERS

General:

*Flower sex.*—Fully developed stamens and fully developed gynoecium.

*Position of first flowering node.*—Between 3rd and 4$^{th}$ node.

*Number of inflorescences per shoot.*—1 to 2: about 1.8.

*Date of full bloom.*—Around November 14$^{th}$, Central valley of Chile.

*Duration of bloom period.*—On average, about 7 days.

*Time of bloom.*—Medium, around November 10$^{th}$, Central valley of Chile.

*Petal number.*—5.

*Petal size, length (mm).*—1.6 mm.

*Petal size, width (mm).*—1.0 mm.

*Color upper and lower petal surface.*—Both upper and lower petal surface present colors 143B and 143C.

*Petal texture.*—Smooth.

*Style length (mm).*—1.4 mm.

*Style color.*—Styles present color N144C.

*Filaments length (mm).*—3.2 mm.

*Filaments color.*—Filaments present colors 1A.

*Anther color.*—Anther present colors 151D.

*Pollen color.*—Pollen present colors 151A and 151B.

FRUIT

General:

*Ripening period.*—Mid-season. Approximately, February 28$^{th}$ in Chile Central Valley.

*Use.*—Fresh market.

*Keeping quality.*—Good.

*Shipping quality.*—Good.

*Solids-sugar.*—Refractometer test about 17.1° Brix.

*% Titratable acidity.*—About 0.26%.

*Sugar/acid ratio.*—47.5.

Cluster:

*Cluster size (peduncle excluded).*—43.5 cm.

*Mature cluster weight.*—About 550 grams.

*Mature cluster length.*—About 20 cm.

*Mature cluster density.*—Very lax.

*Number of berries.*—Between 100-120.

*Form.*—Conical.

Peduncle:

*Length of peduncle.*—About 5 cm.

*Lignification of peduncle.*—Medium.

*Color.*—Yellow-green 145B and 145C.

Berry:

*Size.*—Medium. When treated with gibberellic acid, the average berry size is 16.5 mm width and 18.3 mm length.

*Uniformity of size.*—Uniform.

*Berry weight.*—About 4.1 gram when treated with gibberellic acid.

*Shape.*—Ovoid.

*Presence of seeds.*—Rudimentary.

*Cross-section.*—Circular.

*Dimensions.*—Longitudinal axis about 21 mm; horizontal axis about 18 mm.

*Skin color (without bloom).*—Following colors were observed: Red 40B, Red 43B and Red 47B.

*Flesh color.*—Absent or very weak.

*Juiciness of flesh.*—Slightly juicy.

*Berry firmness.*—Very firm.

*Particular flavor.*—Muscat.

*Bloom (cuticular wax).*—Medium.

*Berry separation from pedicel.*—Moderately easy.

Skin:

*Texture.*—Smooth.

*Reticulation.*—Absent.

*Roughness.*—Absent.

VINE

General:

*Size.*—Large, the average vine size is 1.98 m.

*Vigor.*—Moderate to strongly vigorous.

*Density of foliage.*—Medium.

*Productivity.*—Very productive, about 20 to 24 Kg/vine.

*Rootstock.*—'Harmony' (unpatented).

SHOOTS

Young shoot:

*Form of tip.*—Half open.

*Intensity of anthocyanin coloration of tip.*—Medium.

*Density of prostrate hairs on tip.*—Dense.

*Density of erect hairs on tip.*—Absent or very sparse.

Flowering shoot:

*Attitude during flowering on shoot which are not tied.*—Erect.

*Color of dorsal side of internodes.*—Yellow-green 144B.

*Color of ventral side of internodes.*—Yellow-green 144B.

*Color of dorsal side of node.*—Yellow-green 144A.

*Color of ventral side of nodes.*—Yellow-green 144B.

*Density of erect hairs on nodes.*—Absent or very sparse.

*Erect hairs on internode.*—Absent or very sparse.

*Density of prostrate hairs on nodes.*—Sparse.

*Density of prostrate hairs internodes.*—Sparse.

Woody shoot:

*Internode length.*—Medium, about 8.0 to 13.0 cm.

*Cross section.*—Circular.

*Surface texture.*—Smooth.

*Average woody vine trunk diameter.*—7.76 cm.

*Woody vine trunk has colors.*—201B and 201C.

Tendrils:

*Length of tendrils.*—Short, about 14 to 16 cm.

*Form.*—Trifurcated.

*Number of consecutive tendrils.*—2.

Having thus described and illustrated the new variety of grapevine, I claim:

1. A new and distinct variety of grapevine named 'INIA-G3' as illustrated and described.

* * * * *